United States Patent [19]

Rosen et al.

[11] Patent Number: 4,643,186

[45] Date of Patent: Feb. 17, 1987

[54] PERCUTANEOUS TRANSLUMINAL MICROWAVE CATHETER ANGIOPLASTY

[75] Inventors: Arye Rosen, Cherry Hill, N.J.; Paul Walinsky, Philadelphia, Pa.

[73] Assignee: RCA Corporation, Princeton, N.J.

[21] Appl. No.: 792,852

[22] Filed: Oct. 30, 1985

[51] Int. Cl.⁴ .............................................. A61N 1/32
[52] U.S. Cl. ............................ 128/303.1; 128/303.13; 128/804; 128/784
[58] Field of Search ................... 128/303.1, 362, 784, 128/783, 804, 642

[56] References Cited

U.S. PATENT DOCUMENTS

| | | | |
|---|---|---|---|
| 3,858,586 | 1/1975 | Lessen | 128/303.1 |
| 4,204,549 | 5/1980 | Paglione | 128/784 |
| 4,207,874 | 6/1980 | Choy | 128/303.1 |
| 4,311,154 | 1/1982 | Sterzer | 128/804 |
| 4,409,993 | 10/1983 | Furihata | 128/784 |
| 4,423,989 | 12/1983 | Schjeldhal et al. | 604/104 |
| 4,445,842 | 5/1984 | Hussein et al. | 128/303.1 |
| 4,583,556 | 4/1986 | Hines et al. | 128/804 |

FOREIGN PATENT DOCUMENTS

| | | | |
|---|---|---|---|
| 105677 | 4/1984 | European Pat. Off. | 128/804 |
| 1054194 | 7/1957 | Fed. Rep. of Germany | 128/804 |
| 2815156 | 10/1978 | Fed. Rep. of Germany | 128/804 |
| 624640 | 8/1978 | U.S.S.R. | 128/784 |

OTHER PUBLICATIONS

"The Artery Zapper", Lee Discover, 12/82, pp. 36, 37 & 40.
Abstract entitled "Factors Influencing Trans-Catheter Radio-frequency Ablation of the Myocardium," by Hoit et al. appeared in Circulation magazine, vol. 72, Oct. 1975, of the American Heart Association.
Article "Medical Applications of Microwave Energy" by R. W. Paglione, published beginning at p. 170, RCA Engineer, Sep.-Oct. 1982.
Article "Session 6: Biomedical Aspects of Microwaves" mentions Microwave Catheter Angioplasty on p. 131 of the 1984 IEEE MTT-S Digest.
Article "Catheter Ablation in Dysrhythmas," by Gillette, published at pp. 67-69 of the Mar. 1984 issue of Cardio.
Article "Transvenous Catheter Ablation of a Posteroseptal Accessory Pathway in a Patient with the Wolff-Parkinson-White Syndrome," by Morady et al., published at pp. 705-707 of the Mar. 15, 1984, New England Journal of Medicine Bardex Trademark sample catalog enclosed (pp. 2,3,6 &9).

Primary Examiner—Kyle L. Howell
Assistant Examiner—David Shay
Attorney, Agent, or Firm—Joseph S. Tripoli; Robert L. Troike; William H. Meise

[57] ABSTRACT

Percutaneous transluminal electromagnetic (EM) catheter angioplasty is performed using radio frequency (RF) or microwave frequency power. The catheter includes a coaxial transmission line terminated at its distal end in an antenna. The antenna includes an extension of the coaxial center conductor past the outer conductor. A treatment includes orienting the catheter in the lumen of a cardiac artery adjacent stenotic plaque, and applying sufficient electric power to cause arcing for electroabrasion of the plaque. Another catheter includes a balloon located at the distal end of the the catheter and surrounding the antenna. In use, the balloon is pressurized so as to apply lumen-expanding force against the plaque. The antenna radiates EM energy, heating and softening the plaque, thereby allowing the plaque to be compressed and the stenotic lumen to have increased patency. In another embodiment, a portion of the interior surface of the balloon is metallized so that, when inflated, the metallized surface of the balloon coacts with the antenna to form a reflector.

8 Claims, 13 Drawing Figures

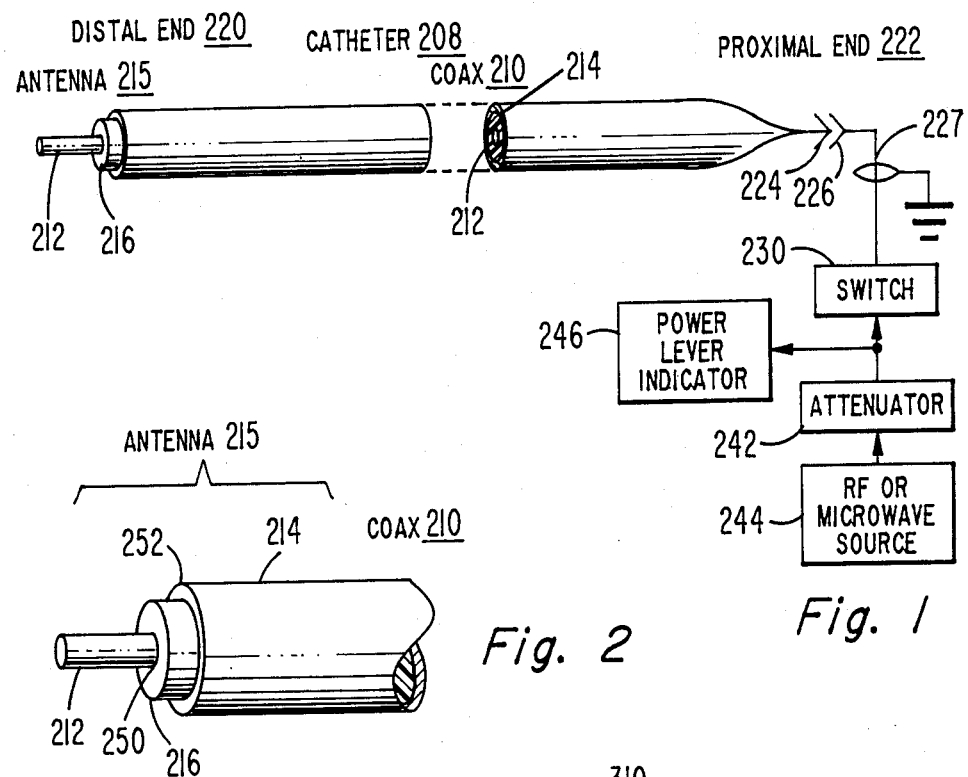
Fig. 1
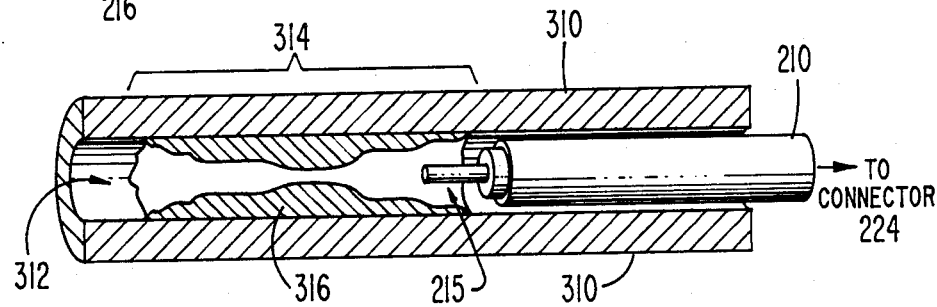
Fig. 2
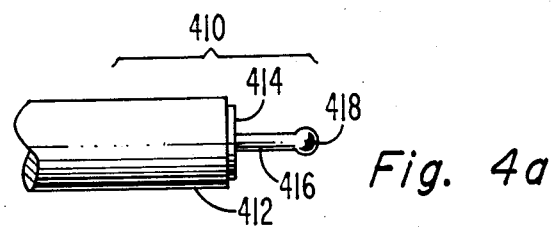
Fig. 3
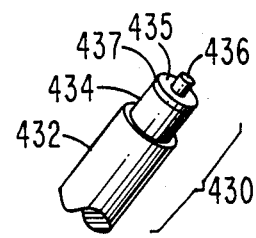
Fig. 4c
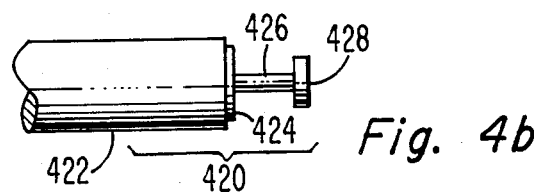
Fig. 4a
Fig. 4b

PERCUTANEOUS TRANSLUMINAL MICROWAVE CATHETER ANGIOPLASTY

This invention relates to the medical procedure of percutaneous transluminal angioplasty by means of a microwave catheter.

BACKGROUND OF THE INVENTION

Several hundred thousand people die suddenly in the United States each year from acute myocardial infarction, and many more suffer from chronic heart problems. A major contributing factor in both acute and chronic heart problems is a reduction in nutrient blood flow to the muscles of the heart resulting from a reduction of blood flow through the coronary blood vessels. The reduction in flow may be caused by deposits of atherosclerotic plaque on the walls of the blood vessel, which causes a narrowing of the lumen or channel of the blood vessel. When the lumen is sufficiently narrowed, the rate of flow of blood may be so diminished that spontaneous formation of a thrombus or clot occurs by a variety of physiologic mechanisms. As is known, once a blood clot has started to develop, it extends within minutes into the surrounding blood, in part because the proteolytic action of thrombin acts on prothrombin normally present, tending to split this into additional thrombin which causes additional clotting. Thus, the presence of atherosclerotic plaque not only reduces the blood flow to the heart muscle which it nourishes, but is a major predisposing factor in coronary thrombosis.

Among the treatments available for the conditions resulting from plaque formations are pharmacological means such the use of drugs, for example nitroglycerin, for dilating the coronary blood vessels to improve flow. In those cases too far advanced to be manageable by drugs, surgical treatment may be indicated. One of the surgical techniques commonly used is the coronary bypass, in which a substitute blood vessel shunts or bypasses blood around the blockage. The bypass operation is effective but is expensive and subject to substantial risks.

Percutaneous transluminal balloon catheter angioplasty is an alternative form of treatment. This method involves insertion of a deflated balloon into the lumen of an artery partially obstructed by plaque, and inflation of the balloon in order to enlarge the lumen. The lumen remains expanded after removal of the catheter. The major problem with this technique is restenosis of the narrowed vessel by recurrence of the arterial plaque.

Another technique which has recently received a good deal of attention is transluminal laser catheter angioplasty. This treatment involves introduction into the coronary artery of a fiber optic cable the proximal end of which is connected to a laser energy source. The distal end of the fiber optic cable is directed towards the plaque. The laser is pulsed, and the resulting high energy light pulse vaporizes a portion of the plaque. Many problems remain unsolved in laser catheter angioplasty. Locating the plaque requires some means such as a fiber optic scope to see the region towards which the laser pulse will be directed. The interior of the artery must be illuminated, and a clear liquid introduced into the artery to displace opaque blood from the region to be viewed. Even with a fiber optic scope, however, the plaque may be difficult to distinguish from normal arterial walls. When the energy of the laser discharge is directed towards the arterial walls, the walls may undesirably be perforated. Further problems relate to the difficulty in matching the characteristic of lasers and fiber optic cables to the frequency absorption characteristics of various types of plaque, and the by-products of the destruction of the plaque.

There is a need for a relatively simple and efficacious technique and apparatus for increasing the patency of a lumen obstructed by plaque.

SUMMARY OF THE INVENTION

A method of treatment for reducing the occlusive effect of plaque located at a point in a vas (tube or channel, as a blood vessel) in tissue, includes the steps of inserting into the vas the end of an elongated electromagnetic transmission line terminated in an antenna. The position of the transmission line is adjusted until the antenna is adjacent the plaque. Radio frequency (RF) or microwave frequency electrical energy is applied to the proximal end of the transmission line whereby the antenna couples energy to the plaque. According to another aspect of the invention, a balloon catheter is inserted into the vas into the region adjacent or surrounding the antenna and is inflated in order to expand the lumen. An apparatus for practicing the method of treatment includes a coaxial transmission line having an antenna at its distal end formed by a protruding center conductor. A balloon surrounds the distal end of the transmission line and the antenna. The material of the balloon is permeable to electromagnetic energy so that the antenna can radiate to the plaque. Another arrangement has a portion of the interior of the balloon metallized so that the balloon, when inflated, acts as a reflector of electromagnetic energy and directs the energy in the desired direction.

DESCRIPTION OF THE DRAWING

FIG. 1 illustrates partially in pictorial and partially in block diagram form a catheter for microwave angioplasty and apparatus for operating the catheter;

FIG. 2 illustrates details of the antenna which terminates the catheter of FIG. 1;

FIG. 3 illustrates the distal end of a catheter such as that illustrated in FIG. 1 inserted into a coronary artery partially occluded by plaque for treatment according to a method of the invention;

FIGS. 4a, 4b and 4c illustrate various antennas suitable for use with the catheter of FIG. 1;

DESCRIPTION OF THE INVENTION

Figure 5A:
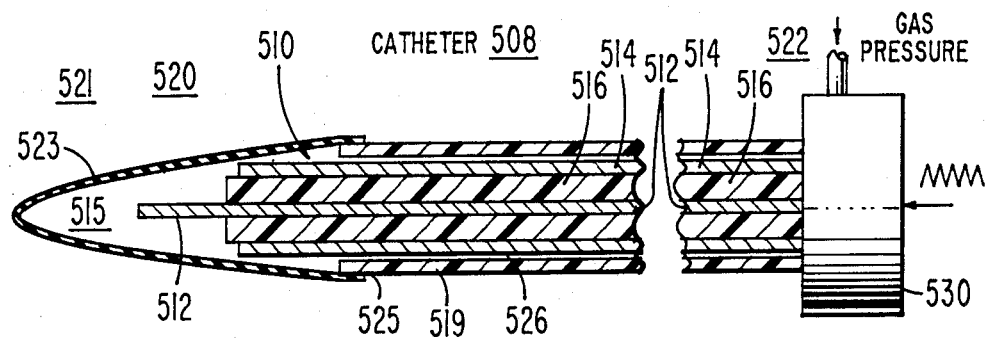
FIG. 5a illustrates a catheter including a coaxial transmission line and an antenna, and a deflated balloon surrounding the antenna.

In FIGS. 1 and 2, a flexible catheter designated generally as 208 includes a flexible coaxial transmission line (coax) 210 including a center conductor 212 coaxial with a cylindrical outer conductor 214. An insulating or dielectric material 216 fills the space between center conductor 212 and outer conductor 214 for holding center conductor 212 and outer conductor 214 in place and for electrically isolating the conductors from each other. A suitable type of coaxial transmission line is Alpha type 9178B having an outer diameter of 0.095 inches (2.413 millimeters). This cable has a braided outer conductor and stranded center conductor and is extremely flexible. The strands of the center and outer conductors may be silver-soldered or brazed together at their distal ends to maintain structural integrity. At the distal end 220 of catheter 208 dielectric material 216 extends somewhat past the distal end of outer conductor 214, and center conductor 212 extends past the end of dielectric material 216. As is well known in the antenna arts, such an arrangement when receiving radio frequency (RF) or microwave frequency electrical energy from the proximal end 222 of coaxial cable 210 radiates electromagnetic energy radially away from the axis of the coax at distal end 220. At its proximal end 222, coax 210 of catheter 208 is coupled by way of standard mating coaxial connectors illustrated as 224 and 226 and through a further coaxial transmission line 227 to a switch illustrated as a block 230. A radio frequency or microwave frequency signal source 244 is coupled by way of a variable attenuator (power reducer) 242 to switch 230. A power level indicator or meter of known type is coupled to the output of attenuator 242 to provide an indication of the amount of electrical power available at the input end of switch 230 for application to catheter 208.

FIG. 3 illustrates in cut-away view a stenotic (narrowed) coronary artery in which the smooth muscle wall is designated 310, defining a lumen 312. Bracketed region 314 defines a stenotic region in which the lumen is partially occluded by either fatty or calcified plaque (deposits). The distal end of catheter 208 including a portion of coax 210 and antenna 215 is inserted transluminally. The position of antenna 215, as illustrated, is near stenotic plaque 316.

A stenotic lumen in region 314 is relieved or opened by a method including percutaneous transluminal (through the skin and the channel of a vessel) introduction of catheter 208 into the artery and locating antenna 215 as near the deposit of plaque as possible. Source 244 is turned on and attenuator 242 is adjusted so as to produce an appropriate power level on indicator 246. Switch 230 is then operated to a closed or conductive condition, allowing energy to flow to catheter 208 and antenna 215 by way of switch 230. At power levels below a certain threshold, antenna 215 radiates electromagnetic energy into the region surrounding the antenna. Above the threshold level arcing occurs. Because of the shape of antenna 215, arcing occurs along a path extending from the region 250 (FIG. 2) at which center conductor 212 exits from insulation 216 to a point on the edge 252 of outer conductor 214. Such arcing causes electroabrasion (electrical removal) of the plaque in the region immediately adjacent to the antenna. This technique is particularly advantageous in the case of calcified plaque which cannot be softened by heating, as described below. Catheter 208 may be advanced through the stenotic region 314 applying power from source 244 and eroding plaque at appropriate positions.

It has been noticed that when electrical energy is applied to an antenna such as antenna 215 of FIGS. 1 and 2 that there is a tendency for a thrombus (blood clot) to form around the protruding center conductor. This effect may be reduced by infusing or introducing through a separate cannula (not illustrated) a physiologically inert and electrically transparent liquid. Such a liquid may be saline solution.

FIG. 4a illustrates the distal end of a catheter in which the antenna region 410 includes an outer conductor 412, insulation 414 protruding slightly therefrom, and a center conductor 416 in which the strands of the protruding portion have been silver soldered together with a bulbous portion 418 at the tip thereof. FIG. 4b illustrates a distal end of a catheter according to the invention in which the antenna region 420 includes an outer conductor 422, insulation 424, a center conductor 426 and a conductive top cap 428. As is known in the antenna art, a bulbous or disc-shaped top cap increases the capacitance between the tip of one of the antenna elements (the protruding center conductor 426) and its reference point (in this case, the distal end of the outer conductor 422), thereby increasing the matching to the antenna element and thereby increasing radiation efficiency across larger volume. The radiation effectiveness of the arrangement of FIG. 4b is generally superior to that of FIG. 4a but is less suitable for use as a catheter because of the likelihood of injury to the patient.

FIG. 4c illustrates an antenna arrangement having the efficient radiation characteristics of the arrangement of FIG. 4b but which is more suitable for catheter use because of the reduced likelihood of injury. In FIG. 4c, an antenna region 430 includes an outer conductor 432 and an insulating portion 434 which protrudes from the distal end of outer conductor 432 almost to the tip of center conductor 436. The end of insulating material 434 defines a disc-shaped plane 435 which is thinly coated with a layer of metal 437 which is in intimate contact with center conductor 436. The layer of metal 437 may be deposited in known fashion, such as by sputtering, on surface 435.

FIG. 5a illustrates a catheter 508 which includes a coaxial cable and an antenna at the distal end thereof and which also includes a balloon surrounding the antenna. In FIG. 5a, catheter 508 includes a coaxial cable 510 having a center conductor illustrated as 512 and an outer conductor 514 separated by a dielectric material 516. An antenna designated generally as 515 is located at distal end 520 of catheter 508 and includes a portion of insulating or dielectric material 514 protruding past the distal end of outer conductor 514, and a portion of center conductor 512 protruding past the distal end of insulating material 516. Coax 510 and antenna 515 are identical to coax 210 and antenna 215 of FIG. 1.

Catheter 508 also includes a flexible jacket 519 which surrounds outer conductor 514. Jacket 519 may be sized so as to provide a space between outer conductor 514 and jacket 519. At the distal end of catheter 508, a balloon designated generally as 521 includes a thin highly flexible membrane 523 which surrounds antenna 515. The os or mouth of balloon 521 makes a gas-tight seal around the periphery of jacket 519 along an annular path 525. Membrane 523 is formed from a material which is essentially transparent to electromagnetic energy, such as a thin latex material.

The method by which electromagnetic energy is radiated as a result of electrical signals applied to the proximal end of coax 510 is explained above in conjunction with FIG. 1. Balloon 521 may be inflated or deflated by gas pressure which may be either positive or negative, and is applied to the interior of the balloon by the channel defined by the region between jacket 519 and insulation 516. Since outer conductor 514 of coax 510 is formed from braided strands, the braiding leaves large numbers of interstices or gaps which form a channel through which gas can flow even if jacket 519 is close fitting about outer conductor 514.

At the proximal end 522 of catheter 508, a connector illustrated as a block 530 provides access to channel 526 and to coax 510 for the flow of electrical energy. Connector 530 is illustrated in more detail in FIGS. 5b and 5c.

Figure 5B:
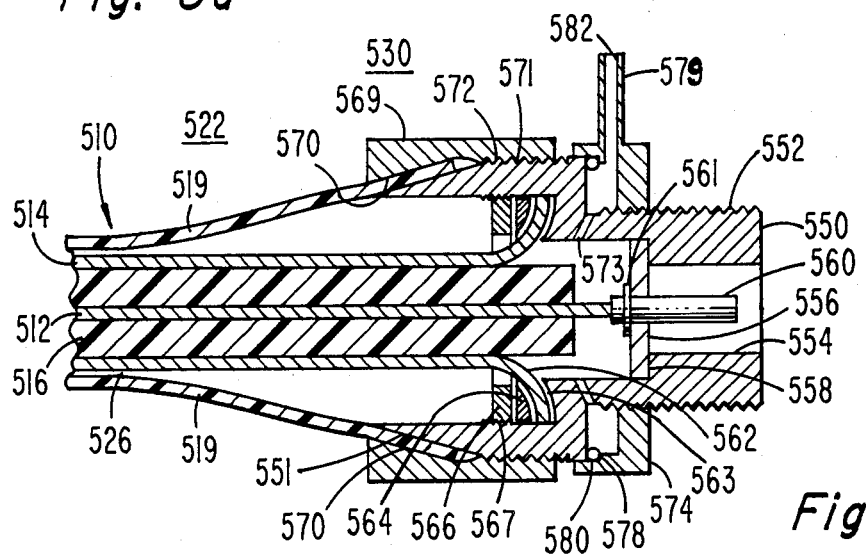
FIG. 5b illustrates in cross-section a connector for the proximal end of the catheter illustrated in FIG. 5a for simultaneously applying electrical signals to the coaxial transmission line and for applying a gas under pressure to the balloon.
Figure 5C:
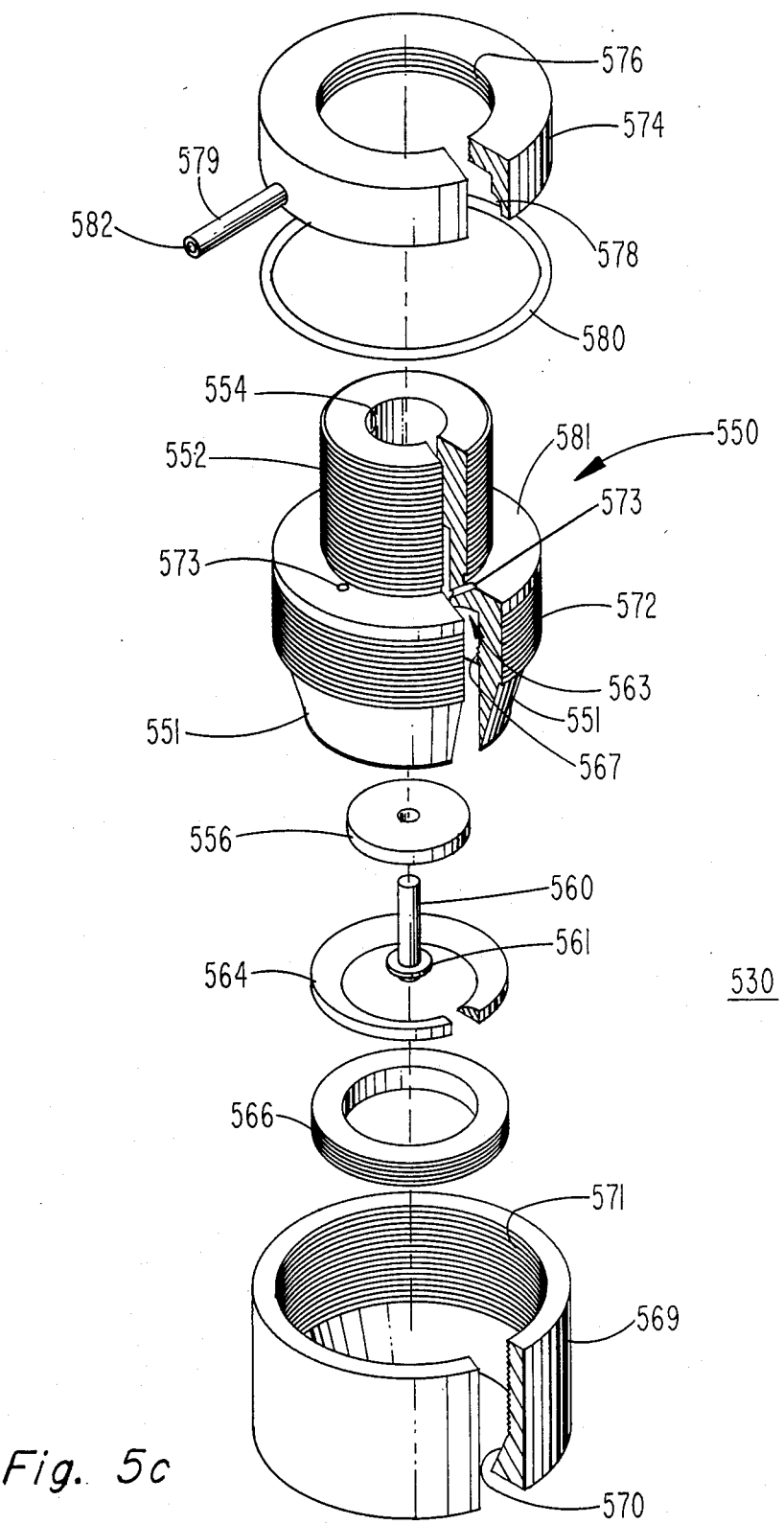
FIG. 5c is an exploded perspective view of the connector of FIG. 5b.

FIG. 5b illustrates in sectional view and FIG. 5c illustrates in exploded view details of connector 530. Functionally, connector 530 must provide a gas-tight connection between a gas source tube and channel 526 through which gas flows to balloon 521. Connector 530 must also provide a transmission-line path between a coaxial connector and the interior of coax 510. In FIG. 5b, connector 530 at proximal end 522 of catheter 508 includes a conductive housing 550 including an externally threaded portion 552 and a bore 554. A gas-impermeable dielectric washer 556 bears against a shoulder 558 of housing 550. The junction between washer 556 and shoulder 558 may include a sealer to aid in preventing the flow of gas. When the interior of the connector is pressurized, washer 556 is forced against shoulder 558. A center conductor connector 560 is slotted to receive a mating male center conductor (not illustrated) and includes a shoulder 561 for bearing against the edge of an aperture in washer 556. The proximal end of center conductor 512 is soldered into a recess (not illustrated) in the end of pin 560. The proximal end of outer conductor 514 is unbraided and flared out to form a curve 562 which fits against a curved shoulder 563 of housing 550. The outer conductor is captivated against shoulder 563 by a ring 566 having a curvature matching that of shoulder 563 and a ring-shaped screw 566 having external threads which mate with an internally threaded portion 567 of housing 550. The connection of jacket 519 to housing 550 is accomplished by flaring the flexible jacket and slipping it over a tapered exterior portion 551 of housing 550. Jacket 519 is captivated against surface 551 by a nut 569 having a tapered interior portion 570 which matches the taper of portion 551 of housing 550. Nut 569 has a threaded portion 571 which engages with threads 572 so as to make a gas tight seal between jacket 519 and housing 550.

In order to introduce gas pressure into the interior of fitting 530, a plurality of holes 573 are drilled through the body of housing 550 near the base of threaded portion 552. A plenum 574 including a threaded aperture 576 and a nipple 579 is screwed over threaded portion 552 of housing 550. Plenum 574 includes a recess 578 adapted to receive an O-ring 580. When plenum 574 is screwed over threaded portion 552 of housing 550 and presses O-ring 580 against surface 581 of housing 550, a chamber is defined which communicates with apertures 573 and with aperture 582 in nipple 579. Naturally, other arrangements are possible for making coaxial connections to coax 510 and gas connections to balloon channel 526.

Figure 6:
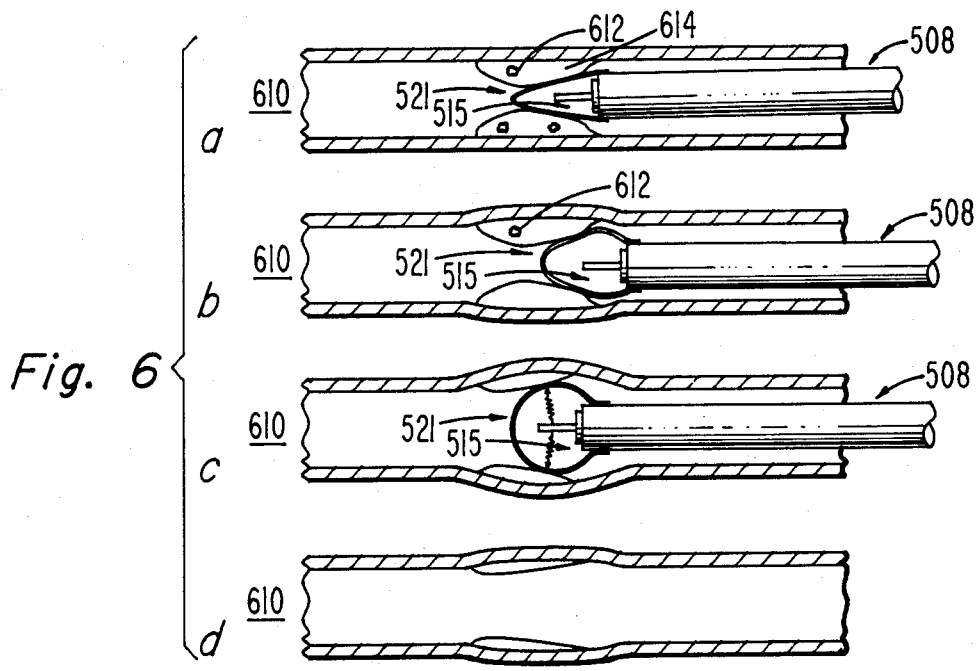
FIGS. 6a–d illustrate in cross-sectional view the catheter of FIG. 5 and a coronary artery partially occluded by plaque during various stages of treatment in accordance with the method of invention.

FIG. 6 illustrates steps in using the catheter of FIG. 5a for angioplasty. In FIG. 6a, catheter 508 with balloon deflated is inserted into the stenotic lumen of a cardiac artery designated generally as 610. Small circles 612 in plaque 614 represent interstices resulting from uneven deposition of the fatty plaque. FIG. 6b represents the result of applying an inflating pressure to balloon 521 by way of the balloon inflating channel of catheter 508. As illustrated, balloon 521 presses against the plaque and on the arterial walls, but because of the sclerotic (hard) nature of the plaque there is little movement. FIG. 6c represents the effect of applying radio frequency or microwave electrical power through the coaxial cable 510 of catheter 508 to antenna 515 at a power level below that required to produce arcing. Electromagnetic energy illustrated by wavy lines is radiated into the plaque, heating and therefore softening it in such a manner as to allow the pressurized balloon to compress interstices 612 and thereby reduce the effective volume of the plaque, and allowing expansion of the stenotic lumen. FIG. 6d illustrates the increased patency of the lumen after the termination of the procedure, including cessation of application of power, deflation of the balloon, and the withdrawal of catheter 508.

It should be noted that an inert liquid need not be introduced into the blood vessel in the region about the antenna when using a catheter such as catheter 508 (FIG. 5a) because blood is not in contact with the antenna when the balloon is inflated and cannot coagulate thereon.

It may be desirable to expand balloon 521 of catheter 521 of a catheter 508 with a dielectric liquid such as water in order to provide a dielectric constant surrounding the antenna which matches that of tissue.

Figure 7A:
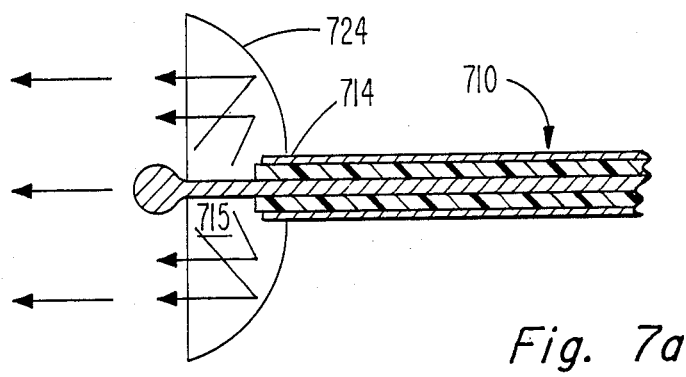
FIG. 7a illustrates the directive effect of a conductive reflector having an approximately spherical shape.
Figure 7B:
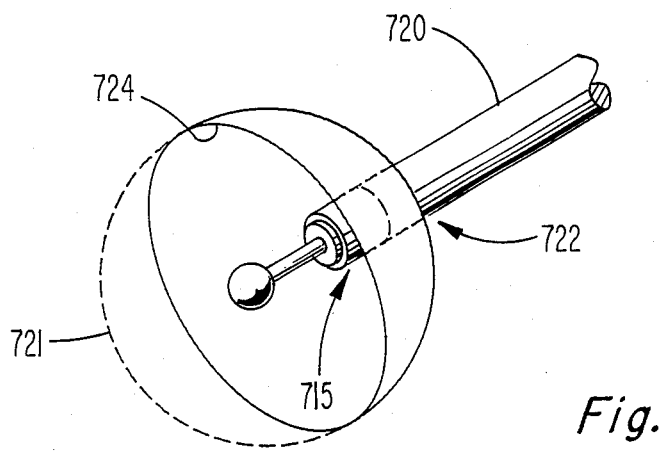
FIG. 7b illustrates partially in phantom view an inflated balloon the inside of which is metalized to form a curved reflector.

FIG. 7a is a simplified cross-sectional representation of a coaxial transmission line 710 and an antenna 715 such as that described in conjunction with FIG. 4a, together with a reflector 720 having the shape of a portion of a sphere. Reflector 720 joins outer conductor 714 of coaxial cable 710. As illustrated by arrows, energy radiated by antenna 715 is directed forwardly, along the axis of coaxial transmission line 710. FIG. 7b illustrates in perspective view a transparent balloon 721 in its inflated condition. Balloon 721 joins outer gas-channel defining jacket 720 at a region 722. Antenna 715 is illustrated at a location inside balloon 721. A metallized surface 724 covers the interior of the proximal hemisphere of balloon 721 to form a reflector similar to reflector 724. Thus, when balloon 721 is inflated, regions anterior to the distal end of the catheter may be heated by electromagnetic power. It should be noted that when the balloon is deflated, metallized surface 724 may short-circuit the center and outer conductor portions of antenna 715, which may prevent heating when the balloon is deflated. This may be avoided by coating the entire surface of antenna 715 including the center conductor and outer conductor with a thin layer of dielectric material or insulation.

Figure 8:
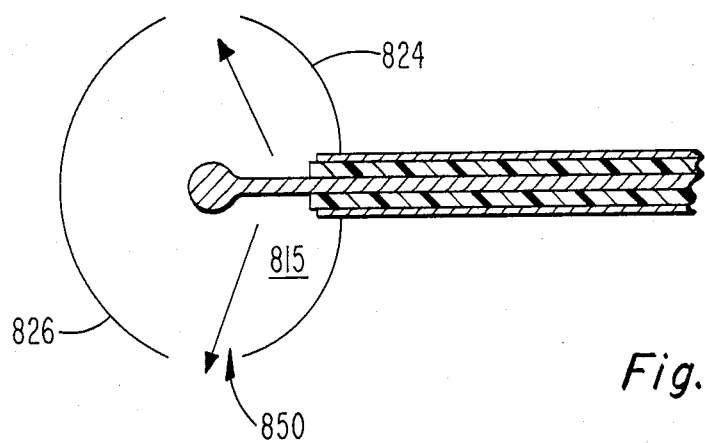
FIG. 8 illustrates the result of metallizing two portions of the surface of the balloon in order to constrain the radiation to an annular slot.

FIG. 8 is a simplified representation of an antenna 815 surrounded by a balloon (balloon material not illustrated) having metallized portions 824 and 826, each of which is not quite a hemisphere, thereby defining an annular opening 850 which limits radiation to those portions of the plaque immediately adjacent to the distal end of the catheter.

Other embodiments of the invention will be obvious to those skilled in the art. In particular, the energy applied from source 244 to catheter 208 may be continuous-wave (CW) or pulse. If desired, the channel for the flow of balloon inflating pressure may be formed within insulation 515 as by axial apertures formed therein. The described catheter may be used in conjunction with other catheters and catheter techniques, as with fiber-optic illuminating, laser, and viewing catheters, fluid infusing and aspirating cannulas, and the like.

What is claimed is:

1. A catheter for percutaneous transluminal angioplasty, comprising:
    a coaxial transmission line having distal and proximal ends and including a center conductor coaxial with an outer conductor;
    an antenna electrically coupled to said distal end of said coaxial transmission line;
    coaxial connecting means coupled to said proximal end of said coaxial transmission line, said coaxial connecting means being adapted for coupling to a source of radio frequency or microwave electrical energy;
    a fluid-tight jacket surrounding said outer conductor and defining a longitudinal channel through which fluid can flow;
    a balloon the os of which is joined to the distal end of said jacket said balloon surrounding and enclosing said antenna, and being formed from a material which is electromagnetically transparent and impermeable to said fluid, a portion of the inside of said balloon being metallized whereby said ballon when inflated acts as a reflector for coacting with said antenna to direct said electromagnetic energy generally in a preferred direction; and
    fluid coupling means coupled to the proximal end of said jacket coupling a source of said fluid under pressure to said balloon by way of said channel for inflation or deflation thereof.

2. A catheter according to claim 1 wherein said metallized portion comprises a region of said balloon near said os, and said preferred direction is along the axis of said catheter.

3. A catheter according to claim 1 wherein said fluid is a gas.

4. A method for reducing the occlusive effect or plaque located at point in a blood vessel in tissue, comprising the steps of:
    obtaining access to the interior of said blood vessel;
    inserting a first end of an elongated electromagnetic transmission line terminated in an antenna into said blood vessel;
    adjusting the position of said transmission line until said antenna is adjacent said point; and
    applying radio frequency or microwave frequency electrical energy to the other end of said transmission line in such an amount that said antenna couples at least a portion of said energy to said plaque for heating thereof without vaporization or death of the underlying tissue.

5. A method for reducing the occlusive effect of plaque located at a point in a blood vessel, comprising the steps of:
    obtaining access to the interior of said blood vessel;
    inserting a first end of an elongated electromagnetic transmission line terminated in an antenna into said blood vessel;
    adjusting the position of said transmission line until said antenna is adjacent said point;
    injecting a physiologically inert and electromagnetically transparent substance into said blood vessel in the vicinity of said antenna; and
    applying radio frequency or microwave frequency energy to other end of said transmission line in such an amount that said antenna couples at least a portion of said energy to said plaque for heating thereof without vaporization or death of the underlying living tissue.

6. A method according to claim 4 wherein said transmission line is a coaxial transmission line.

7. A method for increasing the size of a lumen of a vas partially occluded by plaque, comprising the steps of:
    inserting into the lumen of said vas a catheter arrangement including a balloon catheter and a coaxial transmission line the distal end of which is terminated in an antenna;
    adjusting the position of said antenna and of said balloon to a point adjacent said plaque;
    applying high frequency or microwave electrical power to the proximal end of said coaxial transmission line whereby electromagnetic energy is coupled to said plaque to thereby heat and soften said plaque;
    inflating said balloon so as to expand said lumen;
    ceasing said application of said electrical power;
    deflating said balloon; and
    removing said catheter arrangement.

8. A method according to claim 7 wherein said ceasing step precedes said inflating step.

* * * * *